United States Patent [19] [11] Patent Number: 5,013,352
Markley et al. [45] Date of Patent: May 7, 1991

[54] SUBSTITUTED PYRIDYL-CYCLOHEXANEDIONES AND THEIR HERBICIDAL USES

[75] Inventors: Lowell D. Markley; Christopher T. Hamilton, both of Midland, Mich.; Beth A. Swisher, Fairfield, Calif.; Jacob Secor, Midland, Mich.

[73] Assignee: DowElanco, Indianapolis, Ind.

[21] Appl. No.: 503,201

[22] Filed: Mar. 30, 1990

[51] Int. Cl.$^5$ .............. C07D 401/00; C07D 213/62; C07D 213/69; A01N 43/40
[52] U.S. Cl. .................................... 71/94; 546/261; 546/296; 546/300
[58] Field of Search ................ 546/261, 296, 300; 71/94

[56] References Cited

U.S. PATENT DOCUMENTS

| 4,163,787 | 8/1979 | Malhotra et al. | 514/345 |
| 4,624,696 | 11/1986 | Kell et al. | 71/88 |
| 4,631,081 | 12/1986 | Watson et al. | 71/94 |
| 4,680,400 | 7/1987 | Bird et al. | 546/141 |
| 4,761,172 | 8/1988 | Jahn et al. | 71/88 |
| 4,812,160 | 3/1989 | Jahn et al. | 71/88 |

*Primary Examiner*—Alan L. Rotman
*Attorney, Agent, or Firm*—S. Preston Jones; Ronald G. Brookens

[57] ABSTRACT

The present disclosure is directed to substituted cyclohexanedione compounds, the preparation of said compounds, compositions containing said compounds and the use of said compositions in the selective pre- and postemergent kill and control of grassy weeds in the presence of various crop plants.

27 Claims, No Drawings

SUBSTITUTED PYRIDYL-CYCLOHEXANEDIONES AND THEIR HERBICIDAL USES

FIELD OF THE INVENTION

The present invention is directed to substituted cyclohexanedione compounds, compositions containing said compounds and the use of said compositions in the selective pre- and postemergent kill and control of grassy weeds.

SUMMARY OF THE INVENTION

The present invention is directed to cyclohexanedione compounds corresponding to the formula

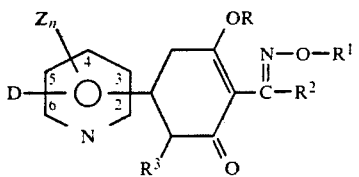

Wherein in this and in subsequent formula depictions, D is a group corresponding to one of the formulae,

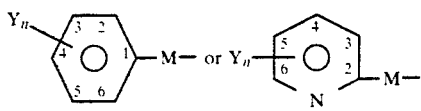

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl:

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl:

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl:

$R^3$ represents hydrogen, $C_1$-$C_4$ alkyl or $C_1$-$C_4$ alkoxycarbonyl:

each Z independently represents hydrogen, halo, $C_1$-$C_4$ alkyl, $C_1$-$C_4$ alkoxy or —$CF_3$;

M represents =O, =S, =S(O) or =S(O)$_2$:

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl: and n represents the integer 1, 2 or 3;

and the herbicidally acceptable organic and inorganic salts thereof.

In addition, the present invention is directed to compositions containing the compounds of Formula I, as an active ingredient therein, and to methods of using said compositions in the selective pre- and postemergent kill and control of grassy weeds, especially in the presence of crop plants such as those hereinafter set forth. The present invention is also directed to a method of preparing the compounds of Formula I.

In the present specification and claims, the term "halo" designates the halogen groups bromo, chloro, fluoro and iodo.

In the present specification and claims, the term "$C_1$-$C_4$ alkyl" designates alkyl groups of 1 to 4 carbon atoms such as, for example, methyl, ethyl, n-propyl, i-propyl, n-butyl, i-butyl, sec.-butyl or t-butyl.

In the present specification and claims, the term "$C_1$-$C_4$ alkoxy" designates alkoxy groups of 1 to 4 carbon atoms such as, for example, methoxy, ethoxy, n-propoxy, i-propoxy, n-butoxy, i-butoxy, sec.-butoxy or t-butoxy.

In the present specification and claims, the term "$C_1$-$C_4$ fluoroalkyl" designates alkyl groups of 1 to 4 carbon atoms substituted with from 1 fluoro atom up to perfluoro substitution.

In the present specification and claims, the term "$C_2$-$C_4$ alkenyl" designates alkenyl groups of 2 to 4 carbon atoms such as, for example, vinyl, allyl, 2-butenyl, 3-butenyl or methallyl.

In the present specification and claims, the term "$C_2$-$C_4$ haloalkenyl" designates alkenyl groups of 2 to 4 carbon atoms substituted with from 1 halo atom up to perhalo substitution.

In the present specification and claims, the term "$C_3$-$C_4$ alkynyl" designates alkynyl groups of 3 or 4 carbon atoms such as, for example, propargyl, 2-butynyl or 3-butynyl.

In the present specification and claims, the term "$C_3$-$C_4$ haloalkynyl" designates alkynyl groups of 3 or 4 carbon atoms substituted with from 1 halo atom up to perhalo substitution.

In the present specification and claims, the term "$C_1$-$C_4$ alkylthio", "$C_1$-$C_4$ alkylsulfinyl" and "$C_1$-$C_4$ alkylsulfonyl" designates alkylthio, alkylsulfinyl and alkylsulfinyl groups of 1 to 4 carbon atoms wherein alkyl is as defined above.

In the present specification and claims, the term "acyl" designates radicals of the formula $R^4$—C(O)— wherein $R^4$ represents $C_1$-$C_4$ alkyl, $C_1$-$C_4$ haloalkyl and phenyl.

The active ingredients of Formula I wherein R represents hydrogen constitutes a preferred embodiment. The active ingredients of Formula I wherein R represents alkyl and $R^2$ represents alkoxy constitutes a more preferred embodiment. The active ingredients of Formula I wherein Y represents alkylthio and alkylsulfonyl constitutes a most preferred embodiment.

In the present invention, it is to be noted that all substituent groups are sterically compatible with each other. The term "sterically compatible" is employed to designate substituent groups which are not affected by steric hindrance as this term is defined in "The Condensed Chemical Dictionary", 7th edition, Reinhold Publishing Co., N.Y. page 893 (1966) which definition is as follows:

"steric hindrance. A characteristic of molecular structure in which the molecules have a spatial arrangement of their atoms such that a given reaction with another molecule is prevented or retarded in rate."

Sterically compatible may be further defined as reacting compounds having substituents whose physical bulk does not require confinement within volumes insufficient for the exercise of their normal behavior as discussed in *Organic Chemistry* of D. J. Cram and G. Hammond, 2nd edition, McGraw-Hill Book Company, N.Y., page 215 (1964).

The cyclohexanediones of the present invention, may exist in either form or in mixtures of the isomeric forms set forth below:

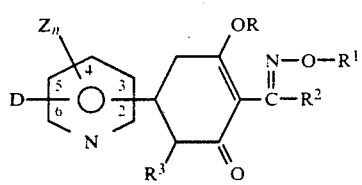

or

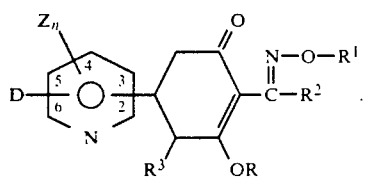

The cyclohexanediones of the present invention, when R is hydrogen, can exist in any of the four tautomeric forms set forth hereinbelow:

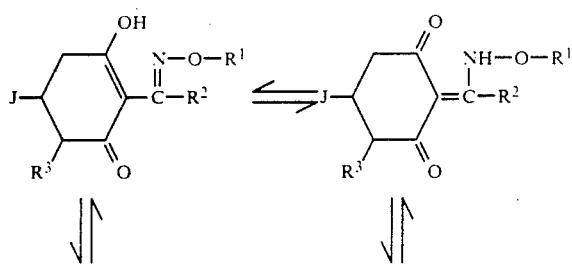

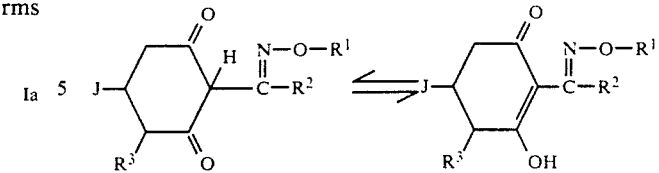

wherein J represents a moiety corresponding to the formula:

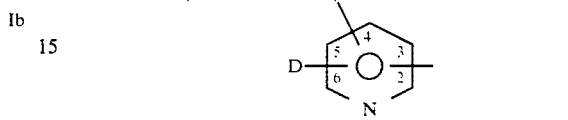

wherein D, Z and n are as hereinabove defined.

The compounds of the present invention are generally low melting crystalline solids at ambient temperatures which are soluble in many organic solvents.

Representative compounds which correspond to Formula I (Compounds of Formulas II and III) include the compounds set forth below in Tables I and II. In the following Tables the middle ring is listed as the prime ‖ | ‖ ring.

TABLE I

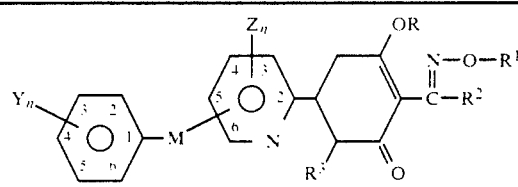

| Y | M | Z | R | R¹ | R² | R³ |
|---|---|---|---|---|---|---|
| 3-F,5-CF₃ | 1,4'-O | —H | —H | methyl | ethyl | —H |
| 3-CH₃S | 1,3'-S | 4'-CH₃O | CH₃SO₂— | Cl—CH₂— | vinyl | —CN |
| 3-F,5-CF₃ | 1,4'-O | —H | —H | n-propyl | ethyl | —H |
| 3-F,5-CF₃ | 1,3'-S | —H | —H | ethyl | ethyl | —H |
| 3,5-Cl₂ | 1,3'-S | 4',6'-Cl₂ | vinyl | ethinyl | phenyl | —Cl |
| 3-Cl,5-CF₃ | 1,3'-O | —H | —H | ethyl | ethyl | —H |
| 3-Cl,5-CF₃ | 1,3'-O | —H | —H | ethyl | methyl | —H |
| 3-F,5-CF₃ | 1,4'-O | —H | —H | ethyl | ethyl | —H |
| 3-F,5-CF₃ | 1,3'-O | —H | —H | ethyl | ethyl | —H |
| 3-Cl,5-CF₃ | 1,3'-S | —H | —H | ethyl | ethyl | —H |
| 3-F,5-CF₃ | 1,3'-O | —H | —H | ethyl | n-propyl | —H |
| 3-F,5-CF₃ | 1,5'-O | —H | —H | ethyl | ethyl | —H |
| 3-Cl,5-CF₃ | 1,4'-O | —H | —H | allyl | ethyl | —H |
| 3-F,5-CF₃ | 1,4'-O | 3',6'-(CH₃)₂ | —H | ethyl | ethyl | —H |
| 2,4-Cl₂ | 1,6'-O | —H | —H | ethyl | ethyl | —H |
| 4-CH₃S | 1,6'-O | —H | —H | ethyl | ethyl | —H |
| 4-CH₃SO | 1,6'-O | —H | —H | ethyl | ethyl | —H |
| 4-CH₃SO₂ | 1,6'-O | —H | —H | ethyl | ethyl | —H |
| 4-CH₃ | 1,6'-S | —H | —H | ethyl | ethyl | —H |
| 2,4-Cl₂ | 1,6'-SO | —H | —H | ethyl | ethyl | —H |
| 2,4-Cl₂ | 1,6'-SO₂ | —H | —H | ethyl | ethyl | —H |
| 2,4-Cl₂ | 1,4'-O | —H | —H | ethyl | ethyl | —H |

TABLE II $$\text{III}$$

| Y | M | Z | R | R¹ | R² | R³ |
|---|---|---|---|---|---|---|
| —H | 2,4'-O | —H | —H | ethyl | ethyl | —H |
| 3-F,5-CF$_3$ | 2,4'-O | —H | —H | ethyl | ethyl | —H |
| 3-F,5-CF$_3$ | 2,4'-S | —H | —H | n-propyl | ethyl | —H |
| 3-Cl,5-CF$_3$ | 2,4'-O | —H | —H | allyl | ethyl | —H |
| 5-CF$_3$ | 3,4'-O | 2',6'-(CH$_3$)$_2$ | —H | ethyl | ethyl | —H |
| 3,5-Cl$_2$ | 2,4'-SO | 2',6'-Cl$_2$ | vinyl | ethinyl | phenyl | —Cl |
| 3-Cl,5-CF$_3$ | 2,5'-O | —H | —H | ethyl | methyl | —H |
| 3,5-CH$_3$ | 2,5'-S | —H | —H | ethyl | ethyl | —H |
| 3-Cl,5-CF$_3$ | 2,5'-O | —H | —H | ethyl | ethyl | —H |
| 3-F | 2,5'-O | —H | —H | ethyl | ethyl | —H |
| 3-F,5-CF$_3$ | 2,5'-O | —H | —H | ethyl | n-propyl | —H |
| 5-CH$_3$ | 2,5'-O | —H | —H | ethyl | ethyl | —H |
| 5-Cl | 2,5'-SO$_2$ | —H | —H | ethyl | ethyl | —H |
| 3-CH$_3$S | 3,5'-S | 3'-methoxy | CH$_3$SO$_2$— | Cl—CH$_2$— | vinyl | —CN |

In the preparation of the compounds of the present invention, the amounts of the reactants to be employed is not critical. In most cases it is preferred to employ substantially equimolar amounts of the reactants. Depending upon the specific type of reaction taking place, it may be beneficial that a given one of the reactants be present in a slight excess to obtain the highest yields of the desired product.

Since the hereinabove and hereinafter set forth compound preparation procedures employ only standard chemistry practices and it is known that slightly different reactants can require slightly different reaction parameters from those for other reactants, it is to be understood that minor modifications to the reaction parameters set forth such as the use of an equivalent solvent, the use of an excess of one of the reactants, the use of a catalyst, the use of high temperature and/or pressure equipment, high speed mixing and other such conventional changes are within the scope of this invention.

The desired product can be separated from the reaction product of the above preparative procedures employing conventional separatory procedures known to those skilled in the art including steps such as, for example, solvent extraction, filtration, water washing, column chromatography, neutralization, acidification, crystallization and distillation.

The compounds corresponding to Formula I of the present invention, wherein R is hydrogen, can be prepared by the reaction of an appropriate ketone reactant, corresponding to Formula IV:

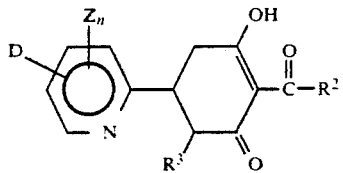

wherein D, Z, R$^2$ and R$^3$ are hereinbefore defined, with an excess of an appropriate alkoxyamine reactant corresponding to the formula R$^1$ONH$_2$ (wherein R$^1$ is as hereinbefore defined) or an inorganic salt thereof and from about 1-2 moles of a base. This reaction can be conducted at temperatures of from about 0° to about 100° C. in the presence of a solvent.

Representative solvents include, for example, dimethyl sulfoxide, C$_1$-C$_4$ alkanols, hydrocarbons, cyclic ethers, halohydrocarbons, and the like, with the C$_1$-C$_4$ alkanols being preferred.

Representative bases include, for example, the carbonates, acetates, alcoholates and hydroxides of the alkali and alkaline earth metals, in particular, sodium and potassium, and organic bases, such as pyridine or tertiary amines, with anhydrous sodium acetate being preferred.

The reaction time can extend for a time of from a few minutes up to 24 hours or more, depending upon the specific reactants and reaction temperature. The product can be recovered employing conventional separatory techniques.

The herbicidally acceptable salts of the compounds of Formula I can be prepared from said compounds employing conventional procedures. The salts are conveniently obtained by mixing an appropriate organic or inorganic base with a compound of Formula I where R is hydrogen, if necessary, in an inert solvent: distilling off the solvent and recrystallizing the residue as necessary.

Representative solvents include, for example, dimethyl sulfoxide, C$_1$-C$_4$ alkanols, hydrocarbons, cyclic ethers, halohydrocarbons, and the like, with the C$_1$-C$_4$ alkanols being preferred.

Representative bases include, for example, the carbonates, acetates, alcoholates and hydroxides of the alkali and alkaline earth metals, in particular, sodium and potassium, and organic bases, such as pyridine or tertiary amines. For ease of formulation, these salts are prepared by neutralization of the above compound of Formula I in an equimolar amount of the base. Other metal salts such as, for example, the manganese, copper, zinc and iron salts can be prepared from the alkali metal salts employing conventional procedures. The ammonium and phosphonium salts can also be obtained employing conventional procedures.

The compounds corresponding to Formula I, wherein R is other than hydrogen, can be prepared by reacting a compound Formula I, wherein R is hydrogen with a compound of the formula R$^a$-L wherein R$^a$ represents $C_1-C_4$ alkyl, $C_1-C_4$ haloalkyl, $C_2-C_4$ alkenyl, $C_3-C_4$ alkynyl, $C_1-C_4$ alkylsulfonyl, phenylsulfonyl or acyl and L is a leaving group such as, for example, chloride, bromide, iodide, nitrate, sulfate, methyl sulfate, tetrafluoroborate, hexafluorophosphate, methanesulfonate, fluorosulfonate and trifluoromethanesulfonate.

The above reaction can be carried out employing the appropriate conventional etherification, acylation or sulfonylation reaction procedures such as taught in U.S. Pat. Nos. 4,631,081 and 4,680,400.

The compounds corresponding to Formula IV can be prepared by the reaction of an appropriate reactant corresponding to Formula V

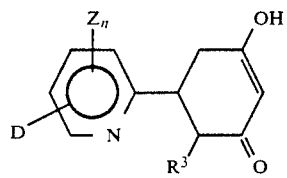

V with an excess of an anhydride corresponding to the formula $(R_2-C=O)_2O$ (wherein $R^2$ is as hereinbefore defined) in the presence of a catalytic amount of a catalyst such as, for example, 4-dimethylaminopyridine and an aprotic solvent, such as, for example, benzene, chloroform and toluene and in the presence of at least a stoichiometric amount of a base such as, for example, pyridine or dimethylaminopyridine.

This reaction is usually carried out by stirring the mixture at ambient temperatures for a period of from about 10 minutes up to about 4 hours and then stirring the mixture under reflux conditions for up to about 6 hours. The mixture is cooled to room temperature, diluted with a solvent such as, for example, diethyl ether and washed with water, followed by a wash with 1N HCl and then dried. The solvent is removed leaving the product as a residue. The product can be purified, if desired, employing conventional techniques.

The compounds corresponding to Formula IV can also be prepared by the reaction of an appropriate compound corresponding to one of the formulae set forth below as D-1,

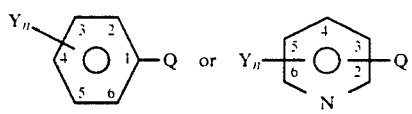

D-1 wherein Q represents halo or methylsulfonyl, with an appropriate cyclohex-2-en-1-one compound corresponding to Formula VI

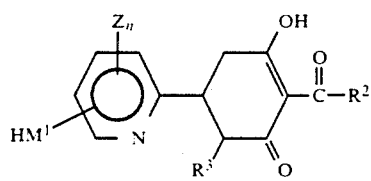

VI wherein $M^1$ is oxygen or sulfur and n is the integer 2 or 3. This reaction can be conducted, with agitation, at temperatures of from about room temperature up to about 140° C. for times of from about 10 minutes up to about 24 hours or more, in the presence of a solvent such as, for example, methyl sulfoxide and a basic material such as, for example, potassium t-butoxide or potassium carbonate. The product can be recovered employing conventional techniques.

The compounds of Formula V can be prepared by the reaction of an appropriate compound corresponding to one of the formulae set forth below as D-2,

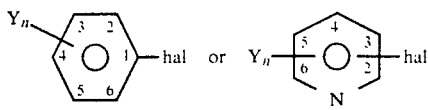

D-2 with an appropriate cyclohex-2-en-1-one compound corresponding to Formula VII

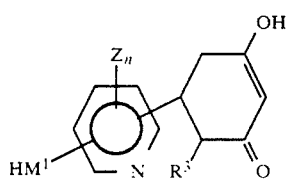

VII wherein $M^1$ is oxygen or sulfur and n is the integer 2 or 3. This reaction can be conducted, with agitation, at temperatures of from about room temperature up to about 140° C. for times of from about 10 minutes up to about 24 hours or more, in the presence of a solvent such as, for example, methyl sulfoxide and a basic material such as, for example, potassium t-butoxide. The product can be recovered employing conventional techniques.

If it is desired that $R^3$ in the compound of Formula V is hydrogen, a mixture of the compound, prepared as above, wherein $R^3$ is alkoxycarbonyl, and 1N sodium hydroxide can be heated at a temperature of from about 50° to about 85° C. for from about 1 up to about 8 hours. The mixture is cooled to room temperature, filtered, the filtrate diluted with water and acidified with a mineral acid to precipitate the desired product. The product, if desired, can be further purified employing conventional procedures.

If it is desired that M in the compounds of Formulae VI and VII, as defined for Formula I, is "SO" or "SO$_2$", the corresponding compound wherein M is "S", as prepared hereinabove, is treated with conventional oxidizing materials such as hydrogen peroxide in acetic acid, m-chlorobenzoic acid and the like using conventional oxidation procedures.

The compounds corresponding to Formula VII when $M^1$ is oxygen and n is the integer 2 or 3 and which are exemplified by the formula

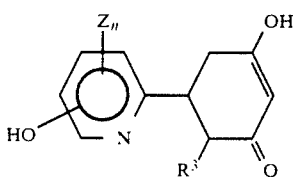

VIIa are known and are taught in U.S. Pat. No. 4,631,081.

The compounds corresponding to Formula VII wherein M is sulfur and n is the integer 2 or 3 and which are exemplified by Formula VIIb can be prepared using the Pummerer rearrangement reaction starting with the treatment of an appropriate compound corresponding to Formula VIIb-1

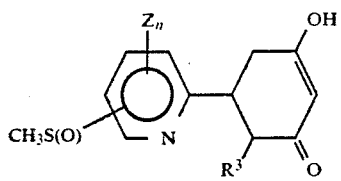   VIIb-1 taught in U.S. Pat. No. 4,631,081.

In carrying out this reaction, the appropriate compound of Formula VIIb-1, at a temperature of about 0° to about 10° C., is slowly added to trifluoroacetic anhydride and the mixture stirred at ambient temperature for from about 1 to about 6 hours. The excess trifluoroacetic anhydride is removed and the residue dissolved in dilute base and this solution stirred at ambient temperature for from about 10 to about 24 hours. The alkaline product can be converted to the H+ form using conventional treatment with an acid.

If it is desired that $R^3$ in the compounds of Formula VIIa and b is hydrogen, a mixture of the compound, prepared as above is converted to the desired form in the same manner as set forth hereinabove for other such compound conversions.

The compounds corresponding to Formula IV wherein $R^3$ is alkoxycarbonyl can also be prepared by admixing an appropriate compound corresponding to Formula VIII

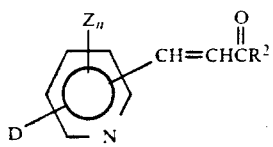   VIII with a solution prepared by mixing equimolar amounts of a solution of a diethyl malonate in an alkanol and a solution of fresh sodium metal dissolved in an alkanol. This mixture is stirred at room temperature for about 24 to about 48 hours or more and then diluted with water and acidified with a mineral acid and extracted with a solvent such as, for example, ethyl acetate or methylene chloride. The organic layer is dried, filtered and concentrated by solvent removal. The mixture is cooled to precipitate the product.

The above compounds corresponding to Formula VIII can be prepared by reacting an appropriate pyridine-aldehyde reactant corresponding to Formula IX,

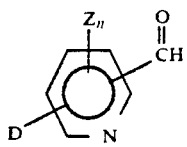   IX with agitation, with acetone in water and a base, for example, the hydroxides of the alkali and alkaline earth metals, in particular, sodium and potassium, and organic bases, such as pyridine or tertiary amines, with sodium hydroxide being preferred or an acetone derivative such as, triphenylphosphoronylidene-2-propanone in benzene or chloroform. The crude product is recovered by filtration and purified by conventional solvent recrystallization.

The above compounds corresponding to Formula IX can be prepared by the reduction of an appropriate ester corresponding to Formula X

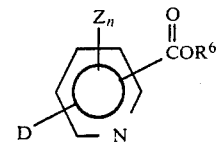   X wherein $R^6$ represents $C_1-C_4$ alkyl. In carrying out this reaction, a solution of the reactant of Formula X, in a solvent such as toluene or hexane is cooled to a temperature in the range of from about $-75°$ to about $-50°$ C. and then a 1 molar solution of diisobutylaluminum hydride (DIBAL-H) in hexane, is slowly added, with stirring. A solution of diethyl ether, glacial acetic acid and water is slowly added to the stirring reaction mixture and stirring is continued until the reaction is complete, as evidenced by the completion of solid formation. The solid is collected and washed thoroughly with diethyl ether. The filtrate is then washed with water, then with sodium bicarbonate and again with water and dried. The solvent is removed under reduced pressure leaving the desired product as a residue.

The compounds corresponding to Formula IX can also be prepared using substantially the same procedure taught in U.S. Pat. No. 4,163,787 in preparing related compounds. In this procedure, an appropriate compound corresponding to one of the formulae set forth below as D-3,

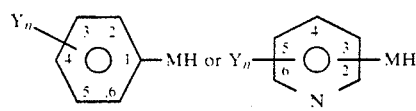   D-3 is reacted with an appropriate halopicolinate compound corresponding to Formula XI

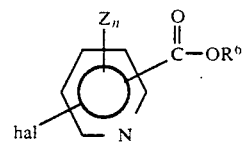   XI

In one such procedure for carrying out this reaction, a slurry of potassium butoxide in a solvent such as diglyme, DMF or DMSO is mixed with a solution of an appropriate compound encompassed by Formulae D-3 and the appropriate halopicolinate encompassed by Formula XI in one of the above solvents. The mixture is refluxed for from 1 to about 4 hours and taken up in a mixture of water and a solvent such as a dialkyl ether. The solvent layer is separated, washed with 1N sodium hydroxide and then with water and dried. The solvent is removed leaving the desired product. If necessary, the product can be purified by conventional treatments such as solvent refining.

The compounds corresponding to Formula XI

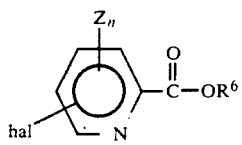

are known and are taught in U.S. Pat. Nos. 4,163,787 and 4,631,081.

The compounds corresponding to Formula VIa which are exemplified by the formula

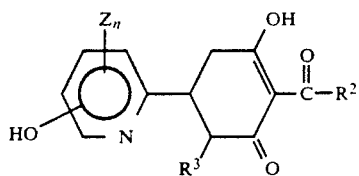

are taught in U.S. Pat. No. 4,631,081.

The following Examples illustrate the present invention and the manner by which it can be practiced, but as such, should not be construed as limitations upon the overall scope of the same.

EXAMPLE I 2-(1-(Ethoxyimino)propyl)-3-hydroxy-5-(6-(4-(methylsulfinyl)phenoxy)-2-pyridyl)cyclohex-2-en-1-one

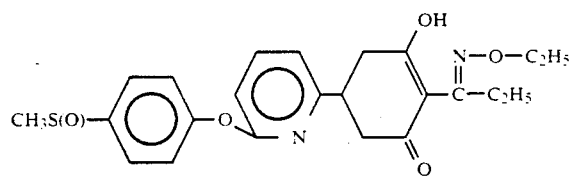

To a solution of 3.1 g (0.00776 mol) of 2--propionyl-3-hydroxy-5-(6-(4-(methylsulfinyl)phenoxy)-2-pyridyl)cyclohex-2-en-1-one in 100 mL of 95 percent ethanol was added 0.98 g (0.0101 mol) of ethoxyamine hydrochloride and 0.95 g (0.0116 mol) of anhydrous sodium acetate. The resulting slurry was stirred for 20 hours at room temperature with sodium chloride precipitating. The mixture was diluted with 150 mL of $CH_2Cl_2$ and with 150 mL of water. The organic layer was separated and washed with water (2×150 mL) and dried over $Na_2SO_4$. Removal of the solvent in vacuo gave 3.4 g of the crude product, which was purified by preparative high-pressure liquid chromatography using a 50:50 mixture of hexane:acetone eluent. The solvent was removed in vacuo to afford 2.6 g (76.5 percent of theoretical) of the above indicated product as a pale yellow oil. $R_f$-0.28 (silica gel, 50:50 acetone-hexane), $^1$H NMR (CDCl$_3$) δ1.1 (t, 3H, CH$_3$CH$_2$—), 1.30 (t, 3H, —OCH$_2$CH$_3$), 2.5-3.6 (m, 7H, ring protons and CH$_3$CH$_2$—), 2.75 (s, 3H, CH$_3$S(O)—), 4.1 (q, 2H, —OCH$_2$CH$_3$), 6.7-7.5 (m,7H, ArH), 14.75 (b, 1H, OH) (Compound 1).

| Analysis: | percent | | |
|---|---|---|---|
| | C | H | N |
| Calc. for $C_{23}H_{26}N_2O_5S$: | 62.42 | 5.92 | 6.33 |
| Found: | 60.66 | 5.94 | 6.12 |

EXAMPLE II 2-(1-(Ethoxyimino)propyl)-3-hydroxy-5-(6-(4-(methylsulfonyl)phenoxy)-2-pyridyl)cyclohex-2-en-1-one

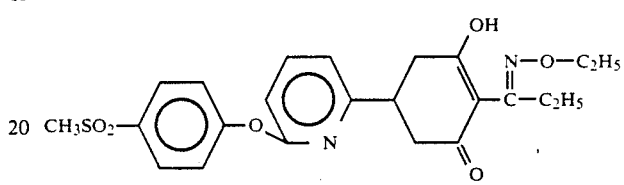

To a slurry of 3.9 g (0.00739 mol) of 2-propionyl-3-hydroxy-5-(6-(4-(methylsulfonyl)phenoxy)-2-pyridyl)-cyclohex-2-en-1-one in 100 mL of 95 percent ethanol was added 1.19 g (0.0122 mol) of ethoxyamine hydrochloride and 1.15 g (0.0141 mol) of anhydrous sodium acetate. The resulting slurry was stirred for 18 hours at room temperature with sodium chloride precipitating. The mixture was diluted with 150 mL of $CH_2Cl_2$ and with 150 mL of water. The organic layer was separated and washed with water (2×150 mL) and dried over $MgSO_4$. Removal of the solvent in vacuo gave 4.3 g of the crude product, which was purified by preparative high-pressure liquid chromatography using a 60:40 mixture of hexane:acetone eluent. The solvent was removed in vacuo to afford 3.25 g (76 percent of theoretical) of the above indicated product as a crystalline solid. The product melted at 80°-82° C.: $R_f$-0.49 (silica gel. 50:50 acetone-hexane), $^1$H NMR (CDCl$_3$): δ1.1 (t, 3H, CH$_3$CH$_2$—), 1.3 (t, 3H, —OCH$_2$CH$_3$), 2.5-3.65 (m, 7H, ring protons and CH$_3$CH$_2$—), 3.1 (s, 3H, CH$_3$SO$_2$—), 6.7-8.1 (m,7H, ArH), 14.75 (b, 1H, OH) (Compound 2).

| Analysis: | percent | | |
|---|---|---|---|
| | C | H | N |
| Calc. for $C_{23}H_{26}N_2O_6S$: | 60.24 | 5.72 | 6.11 |
| Found: | 60.20 | 5.78 | 6.08 |

By following the hereinabove procedures of Examples I and II employing the appropriate starting cyclohex-2-en-1-one and amine reactants, the following compounds in Table III are prepared.

TABLE III

| Cmpd. No. | COMPOUND | M.P. °C. | Mol. Formula | Elem. Analysis | | |
|---|---|---|---|---|---|---|
| | | | | C | H | N |
| 3 | [structure] | Oil | $C_{22}H_{22}Cl_2N_2O_4$ | Calc'd 58.80 Found 58.36 | 4.94 4.90 | 6.24 6.10 |

TABLE III-continued

| Cmpd. No. | COMPOUND | M.P. °C. | Mol. Formula | Elem. Analysis C | H | N |
|---|---|---|---|---|---|---|
| 4 | 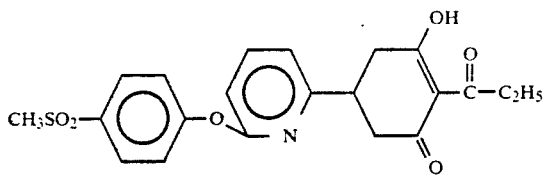 | Oil | $C_{23}H_{26}N_2O_4S$ | Calc'd 64.76<br>Found 63.74 | 6.14<br>6.12 | 6.57<br>6.45 |
| 5 | 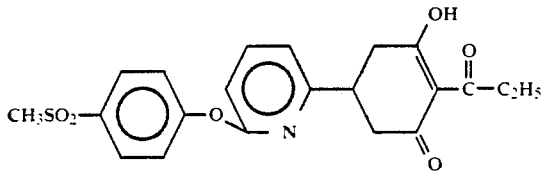 | 87-88 | $C_{23}H_{26}N_2O_3S$ | Calc'd 67.29<br>Found 67.31 | 6.38<br>6.29 | 6.82<br>6.78 |

EXAMPLE III

2-Propionyl-3-hydroxy-5-(6-(4-(methylsulfinyl)phenoxy)-2-pyridyl)cyclohex-2-en-1-one To a solution of 5.5 g (0.0143 mol) of 2-propionyl-3-hydroxy-5-(6-(4-(methylthio)phenoxy)-2-pyridyl)cyclohex-2-en-1-one in 250 mL of methanol was added a solution of 3.22 g (0.0151 mol) of sodium periodate in 25 mL of water. The resulting mixture was stirred at ambient temperature for 24 hours and the sodium iodate by-product was filtered off. The filtrate was reduced in vacuo and the residue dissolved in 150 mL of $CH_2Cl_2$ and washed with water (3×150 mL) and dried over $Na_2SO_4$ and the solvent removed in vacuo. The crude product was dissolved in $CH_2Cl_2$ and placed on a column of silica gel. The column was initially eluted with $CH_2Cl_2$ and then with a 90:10 $CH_2Cl_2$:acetone mixture. The product fractions were combined and the solvent removed in vacuo giving the above named product in a yield of 3.2 g (56 percent of theoretical). The product melted at 78°-86° C.: $R_f$-0.24 (silica gel, 5:95 methanol:$CH_2Cl_2$), $^1H$ NMR (CDCl$_3$) δ1.1 (t, 3H, $CH_3CH_2$—), 2.5-3.6 (m, 7H, ring protons and $CH_3CH_2$—), 2.72 (s, 3H, $CH_3S(O)$—), 6.7-7.8 (m, 7H, ArH), 18.0 (s, 1H, OH).

EXAMPLE IV

2-Propionyl-3-hydroxy-5-(6-(4(methylsulfonyl)phenoxy)-2-pyridyl)cyclohex-2-en-1-one To a solution of 5.8 g (0.0151 mol) of 2-propionyl-3-hydroxy-5-(6-(4-(methylthio)phenoxy)-2-pyridyl)cyclohex-2-en-1-one in 100 mL of $CH_2Cl_2$ cooled to 5° C. in an ice-water bath was added dropwise over 1 hour, a solution of 6.53 g of 80-90 percent m-chloroperbenzoic acid dissolved in 125 mL of $CH_2Cl_2$. The resulting mixture was stirred at ambient temperature for 1.5 hours and the m-chlorobenzoic acid by-product was filtered off. The filtrate was reduced in vacuo leaving a mixture of product and additional m-chlorobenzoic acid. The residue dissolved in $CH_2Cl_2$ and placed on a column of silica gel. The column was initially eluted with $CH_2Cl_2$ and then with a 95:5 $CH_2Cl_2$:acetone mixture. The product fractions were combined and the solvent removed in vacuo giving the above named product, which crystallized on standing. Recrystallization from 95 percent ethanol gave pure product in a yield of 4.9 g. The product melted at 114°-116° C.: $R_f$-0.41 (silica gel, 5:95 methanol-$CH_2Cl_2$), $^1H$ NMR (CDCl$_3$) δ1.10 (t, 3H, $CH_3CH_2$—), 2.5-3.6 (m, 7H, ring protons and $CH_3CH_2$—) 3.1 (s, 3H, $CH_3S(O)_2$—), 6.75-8.05 (m, 7H, ArH), 18.0 (b, 1H, OH).

| Analysis: | percent | | |
|---|---|---|---|
| | C | H | N |
| Calc. for $C_{21}H_{21}NO_6S$: | 60.71 | 5.10 | 3.37 |
| Found: | 60.7 | 5.02 | 3.28 |

EXAMPLE V

2-Propionyl-3-hydroxy-5-(6-(4-(methylthio)phenoxy)-2-pyridyl)cyclohex-2-en-1-one

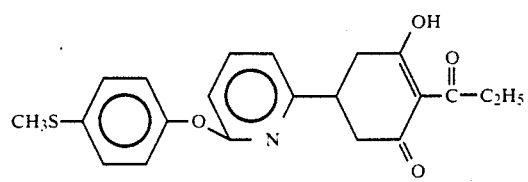

To a slurry of 24.0 g (0.0733 mol) of 3-hydroxy-5-(6-(4-(methylthio)phenoxy)-2-pyridyl) cyclohex-2-en-1-one in 250 mL of benzene was added 10.5 g (0.0806 mol) of propionic anhydride and 17.9 g (0.0147 mol) of 4-dimethylaminopyridine. The mixture was stirred at room temperature for 1 hour and heated at reflux for 4 hours. The reaction mixture was cooled to room temperature and diluted with 150 mL of diethyl ether, washed with 200 mL of water, then washed twice with 150 mL portions of 1N HCl and dried over MgSO$_4$. The solvent was removed in vacuo leaving 28.1 g (100 percent of theoretical) of the above named compound, as the crude product. The product was purified by dissolving it in dichloromethane and passing it through a silica gel column using dichloromethane as the eluent. The product fractions were combined and the desired product was recovered by recrystallization from 95 percent ethanol gave the above named product in a yield of 13.6 g (48 percent of theoretical). The product melted at 54°–56° C.: R$_f$-0.48 (silica gel, 3:97 methanol:-hexane), $^1$H NMR (CDCl$_3$) δ1.1 (t, 3H, —CH$_2$C$\underline{H}_3$), 2.40 (s, 3H, CH$_3$S—), 2.4-3.55 (m, 7H, ring protons and —C$\underline{H}_2$CH$_3$), 6.5-7.7 (m, 7H, ArH), 18.0 (s, 1H, —OH).

EXAMPLE VI

3-Hydroxy-5-(6-(4-(methylthio)phenoxy)-2-pyridyl)cyclohex-2-en-1-one

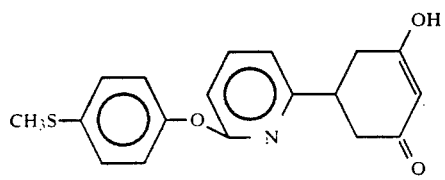

A mixture of 4.33 g (0.029 mol) of 3-hydroxy-5-((6-(4-(methythio)phenoxy)-2-pyridinyl)-4-carboethoxy)cyclohex-2-en-1-one in 435 mL (0.435 mol) of 1N NaOH was heated at 60° C. for 4 hours and cooled to room temperature. The solution was filtered and the filtrate acidified with 45 mL of concentrated HCl and the desired product precipitated out of the solution as an oilysolid. The residue was dissolved in 400 mL of methylene chloride, washed with water, dried over Na$_2$SO$_4$. The solvent was removed in vacuo leaving the product as a crystalline solid in a yield of 32.8 g (92.9 percent of theoretical). The product melted at 137°–141° C.; R$_f$-0.39 silica gel, 75:25 ethyl acetate-hexane + 1 percent AcOH), $^1$H NMR (D$_6$-DMSO): δ2.5 (s, 3H, C$\underline{H}_3$S—), 2.35-3.6 (m, 7H, ring protons), 5.25 (s, 1H, =CH), 6.75-7.9 (m, 7H, ArH), 10.5 (b, 1H, OH).

| Analysis: | percent | | |
|---|---|---|---|
| | C | H | N |
| Calc. for C$_{18}$H$_{17}$NO$_3$S: | 66.03 | 5.23 | 4.28 |
| Found: | 65.9 | 5.29 | 4.02 |

EXAMPLE VII

3-Hydroxy-5-((6-(4-(methylthio)phenoxy)-2-pyridyl)-4-carboethoxy)cyclohex-2-en-1-one

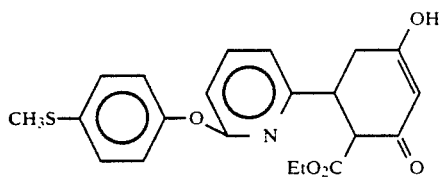

To a solution of 2.62 g (0.114 mol) of freshly cut sodium metal dissolved in 150 mL of absolute ethanol was added a solution of 18.3 g (0.114 mol) of diethyl malonate in 25 mL of absolute ethanol. To this mixture was added a solution of 31.0 g (0.109 mol) of 1-(6-(4-(methylthio)phenoxy)-2-pyridyl)-1-buten-3-one in 100 mL of absolute ethanol. The mixture was stirred at ambient temperature for 24 hours and a white solid precipitated from the solution. The mixture was then diluted with 500 mL of water and the solid slowly dissolved therein. To this solution was slowly added 12 mL of concentrated HCl and the desired product precipitated out of the solution as an oil. The oil was dissolved in 300 mL of methylene chloride and the organic layer was washed with water and dried over Na$_2$SO$_4$. The solvent was removed in vacuo leaving 43.5 g (100 percent of theoretical) of the product as a pale yellow oil: R$_f$-0.39 + 0.51, diasteriomers (silica gel, 75:25 ethyl acetate-hexane + 1 percent AcOH), $^1$H NMR (CDCl$_3$): δ1.3 (t, 3H, C$\underline{H}_3$CH$_2$—), 2.5 (s, 3H, C$\underline{H}_3$S—), 2.5-3.85 (m, 4H, ring protons), 4.2 (q, 3H, CH$_3$C$\underline{H}_2$—), 5.8 (b, 1H, =CH), 6.5-7.7 (m, 7H, ArH), 12.2 (s, 1H, OH).

EXAMPLE VIII 1-((6-(4-(Methylthio)phenoxy)-2-pyridyl)-1-buten-3-one

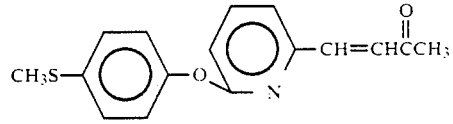

A mixture of 29.9 g (0.122 mol) of 6-(4-(methylthio)-phenoxy)picolinaldehyde and 42.7 g (0.134 mol) of triphenylphosphoranylidene-2-propanone in 750 mL of benzene was heated at reflux for 2.75 hours and cooled. The solvent was removed in vacuo leaving 77 g of an oily solid which was dissolved in methylene chloride and placed on a column of dry silica gel. The column was eluted with methylene chloride and the fractions containing the desired product were combined. The solvent was removed in vacuo leaving 32.5 g (93.7 percent of theoretical) of an oily product which slowly crystallized upon standing. The above named product melted at 71°–72.5° C.; R$_f$-0.53, (silica gel, 50:50 ethyl acetate-hexane), $^1$H NMR (CDCl$_3$) δ2.25 (s, 3H, C$\underline{H}_3$C(O)—), 2.4 (s, 3H, CH$_3$S—) 6.7-7.75 (m, 9H, ArH and —CH=CH—).

| Analysis: | percent | | |
|---|---|---|---|
| | C | H | N |
| Calc. for C$_{16}$H$_{15}$NO$_2$S: | 67.34 | 5.30 | 4.91 |
| Found: | 67.4 | 5.32 | 4.90 |

EXAMPLE IX 6-(4-(Methylthio)phenoxy)picolinaldehyde

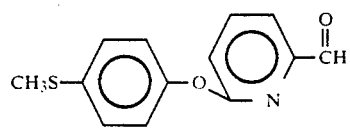

A solution of 38.7 g (0.141 mol) of methyl 6-(4-(methylthio)phenoxy)picolinate in 250 mL of toluene was cooled to a minus 70° C. in a dry ice-acetone bath. To the thus prepared slurry was added dropwise 285 mL of 1 Molar DIBAL-H in hexane over 1.5 hours. The solution was stirred at minus 70° C. for 20 minutes and an additional 20 mL of 1 Molar DIBAL-H in hexane was added. After 15 minutes, a solution of 187.5 mL of diether ether, 62.5 mL of glacial acetic acid and 15 mL of water was added dropwise over 1.5 hours at minus 65° C. with a white solid forming. The thus formed slurry was allowed to stir at ambient temperature overnight and the white solid was collected by filtration and washed with diether ether. The filtrate was washed thrice with 250 mL portions of water followed by washing with 250 mL of a 10 percent sodium bicarbonate solution and then with 250 mL of water. The organic layer was then dried over sodium sulfate and the solvent removed in vacuo leaving 32.4 g (94.1 percent of theoretical) of the above named compound, a white crystalline solid, melting at 60° –63° C.; $^1$H NMR (CDCl$_3$) δ2.40 (s, 3H, CH$_3$S—), 6.9–7.9 (m, 7H, ArH),9.75 (s, 1H, —CH=O).

EXAMPLE X

Methyl 6-(4-(methylthio)phenoxy)picolinate

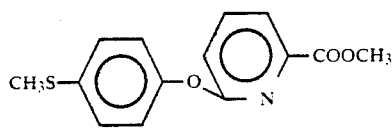

To a slurry of 32.6 g (0.291 mol) of potassium t-butoxide in 250 mL of diglyme was added a solution of 40.9 g (0.291 mol) of 4-(methylthio)phenol in 250 mL of diglyme. To this mixture was added 50 g (0.291 mol) of methyl 6-chloro picolinate and 125 mL of diglyme. The thus formed slurry was heated at reflux for 2.5 hours. The reaction mixture was cooled and 500 mL of diethyl ether and 800 mL of water were added thereto. The diethyl ether layer was separated and washed with 250 mL of 1N NaOH solution followed by three washings with 250 mL portions of water. The layer was dried over sodium sulfate and the solvent removed in vacuo leaving 71.3 g of the crude compound as a tacky solid. The crude was slurried in 300 mL of water, filtered and washed with water and dried leaving 53.3 g of the product. This crude material was slurried in diethyl ether, filtered and washed with additional diethyl ether leaving 39.9 g (49.8 percent of theoretical) of the desired compound, melting at 95°–97° C.; R$_f$-02.8 (silica gel, 25:75 ethyl acetate-hexane), $^1$H NMR (CDCl$_3$) δ2.45 (s, 3H, CH$_3$S—), 3.90 (s, 3H, —OCH$_3$), 6.85-7.9 (m, 7H, ArH).

The compounds of the present invention have been found to be suitable for use in methods for the pre- and postemergent control of many annual and perennial grassy weeds. In addition, the present compounds are sufficiently tolerant toward most broadleaf and some grass crops, such as, for example, soybeans, cotton, sugar beets, corn, rice and wheat, to allow for the postemergent control of grassy weeds growing among said crops.

It is to be noted that while all compounds have herbicidal activity, each compound/active ingredient may have a slightly different effect on different plants. Some compounds will be more active in the control of one weed species than another and some compounds may be more selective toward one crop species than another. Many of these compounds are unique because of their systemic action and because of the very low levels of chemical required to control the grassy weeds.

For such uses, unmodified active ingredients of the present invention can be employed. However, the compounds may be prepared in formulations/compositions as dusts, wettable powders, flowable concentrates, or emulsifiable concentrates by the admixture of the active compounds with inert materials, known in the art as inert agricultural adjuvants and/or carriers, in solid or liquid form.

Thus, for example, the active compound(s) can be admixed with one or more additives including organic solvents, petroleum distillates, water or other liquid carriers, surface active dispersing agents, and finely divided inert solids. For example, an active ingredient can be dispersed on a finely-divided solid and employed herein as a dust or granule. Also, the active ingredients, as liquid concentrates or solid compositions comprising one or more of the active ingredients, can be dispersed in water, typically with aid of a wetting agent, and the resulting aqueous dispersion employed as a spray. In other procedures, the active ingredients can be employed as a constituent of organic liquid compositions, oil-in-water and water-in-oil emulsions or water dispersions, with or without the addition of wetting, dispersing, or emulsifying agents.

The herbicidally effective concentration of the active ingredients in solid or liquid compositions generally is from about 0.0003 to about 95 percent by weight or more. Concentrations from about 0.05 to about 50 percent by weight are often employed.

The compound can be employed in the form of diluted flowable compositions or a wettable powder composition containing 2 to 10,000 ppm of one or more of the compounds, preferably 10 to 600 ppm are employed. When the carrier contains a surface agent, from about 0.1 to about 20 percent by weight of the active ingredient is advantageously employed. Depending upon the concentration in the composition, such augmented compositions are adapted to be employed for the control of the undesirable plants or employed as concentrates and subsequently diluted with additional inert carrier, e.g. water, to produce the ultimate treating compositions.

Similarly, the toxicant products can be compounded with a suitable water-immiscible inert organic liquid and a surface active dispersing agent to produce an emulsifiable concentrate which can be further diluted with water and oil to form spray mixtures in the form of oil-in-water emulsions which may optionally contain water miscible organic co-solvents to improve the physical properties of the formulation. In such compositions, the carrier comprises an aqueous emulsion, i.e., a mixture of inert water-immiscible solvent and optional water miscible organic co-solvent, emulsifying agent, and water. In such compositions, the active ingredient is usually present in a concentration from about 5 to about 98 weight percent.

In the preparation of dust, or wettable powder compositions, the toxicant products can be compounded with any of the finely divided solids, such as prophyllite, talc, chalk, gypsum, fuller's earth, bentonite, attapulgite, starch, casein, gluten, or the like. In such operations, the finely divided carrier is ground or mixed with the toxicant or wet with a solution of the toxicant in a volatile organic solvent. Also, such compositions when employed as concentrates can be dispersed in water, with or without the aid of dispersing agents to form spray mixtures. With dusts, good results can usually be obtained employing compositions containing from about 0.1 to about 2.0 percent or more by weight of toxicant.

Granular formulations are usually prepared by impregnating a solution of the toxicant in a volatile organic solvent onto a bed of coarsely divided attapulgite, bentonite, diatomite, or the like.

Emulsifiers which can be advantageously employed herein can be readily determined by those skilled in the art and include various nonionic, anionic and cationic emulsifiers, or a blend of two or more of said emulsifiers.

Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxide or mixtures of ethylene and propylene oxides such as the ethoxylated alkyl phenols and carboxylic esters solubilized with the polyol or polyoxyalkylene.

Anionic emulsifiers include the oil-soluble salts (e.g., calcium) of alkylaryl sulphonic acids, oil soluble salts of sulphated polyglycol ethers and appropriate salts of phosphated polyglycol ether. Cationic emulsifiers include quaternary ammonium compounds and fatty amines.

The preferred emulsifiers will depend upon the nature of the emulsifiable concentrate. For example, an emulsifiable concentrate of a compound of Formula I containing 200 g/L of the compound in xylene may require a blend of an ethoxylated nonyl phenol and calcium dodecyl benzene sulphonate to function effectively whereas a similar emulsifiable concentrate of the oleate salt of a compound of Formula I soluble in an aliphatic organic solvent will require a considerably different emulsification system.

Representative organic liquids which can be employed in preparing the emulsifiable concentrates of the present invention are the aromatic liquids such as xylene; propyl benzene fractions; or mixed naphthalene fractions: mineral oils substituted aromatic organic liquids such as dioctyl phthalate; kerosene; butene; dialkyl amides of various fatty acids, particularly the dimethyl amides of fatty glycols and glycol derivatives such as the n-butyl ether, ethyl ether or methyl ether of diethylene glycol, the methyl ether of triethylene glycol. Mixtures of two or more organic liquids are also often suitably employed in the preparation of the emulsifiable concentrate. The preferred organic liquids are xylene, and propyl benzene fractions, with xylene being most preferred.

The surface active dispersing agents are usually employed in liquid compositions and in the amount of from 0.1 to 20 percent by weight of the combined weight of the dispersing agent and active compound.

Especially, these active compositions may contain adjuvant surfactants to enhance the deposition, wetting and penetration of the composition onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters of sulphosuccinic acids, ethoxylated organosilicones, ethoxylated fatty amines and blends of surfactant with mineral or vegetable oils.

In further embodiments, the compounds of the present invention or compositions containing the same, can be advantageously employed in combination with one or more additional pesticidal compounds. Such additional pesticidal compounds may be insecticides, nematocides, miticides, arthropodicides, herbicides, fungicides or bactericides that are compatible with the compounds of the present invention in the medium selected for application and not antagonistic to the activity of the present compounds. Accordingly, in such embodiments, the pesticidal compound is employed as a supplemental toxicant for the same or for a different pesticidal use or as an additament. The compounds in combination can generally be present in a ratio of from 1 to 100 parts of the compound of the present invention with from 100 to 1 part of the additional compound(s).

The active ingredients of the present invention have been found to possess desirable postemergent activity against grassy weeds such as foxtail, barnyard grass, wild oat, Johnson grass and the like, while showing high selectivity to important broadleaf crops such as cotton, sunflower sugarbeet, rape and soybeans. These compounds are also uniquely effective in selectively controlling perennial grassy weeds such as Johnson grass and the like in the presence of said crop plants.

The exact amount of the active material to be applied is dependent not only on the specific active ingredient being applied, but also on the particular action desired, the plant species to be controlled and the stage of growth thereof as well as the part of the plant to be contacted with the toxic active ingredient. Thus, all of the active ingredients of the present invention and compositions containing the same may not be equally effective at similar concentrations or be equally effective against the same plant species.

In preemergent operations a dosage rate of 0.01 to 10 lbs/acre (0.011 to 11.2 kgs/hectare), preferably 0.05 to 2.0 lbs/acre (0.056 to 2.25 kgs/hectare) and most preferably 0.1 to 1 lb/acre (0.11 to 1.12 kgs/hectare) is generally employed.

In postemergent operations a dosage of about 0.01 to about 20 lbs/acre (0.056-22.4 kg/hectare) is generally applicable, although not all compounds are equally effective and some weeds are more difficult to control. Thus, a dosage rate in the range of about 0.05 to about 1.0 lb/acre (0.01-1.12 kg/hectare) is preferred in postemergent control of annual grassy weeds, while about 0.05 to about 5 lbs/acre (0.056-5.6 kg/hectare) is a preferred dosage range for the postemergent control of perennial grassy weeds. In applications to tolerant crops a weed controlling but less than crop damaging amount of from about 0.005 to about 1.0 lb/acre (0.0056 to 1.12 kgs/hectare) is generally employed.

Representative formulations/compositions of the present invention include the following:

Emulsifiable Concentrate

TABLE IV

| Ingredient | weight percent of total composition |
|---|---|
| Compound No. 3 | 6.4 |
| Atlox TM 3454$^a$ | 5.4 |
| Atlox TM 3413$^a$ | 5.4 |
| Aromatic 100 | 41.4 |
| Cyclohexanone | 41.4 |

TABLE V

| Ingredient | weight percent of total composition |
|---|---|
| Compound No. 4 | 5.0 |
| Xylene | 65.0 |
| Hallcomid TM M8-10[b] | 20.0 |
| Tenseofix TM B7453[c] | 3.0 |
| Tenseofix TM B7453[c] | 3.0 |
| Ethomeen TM C25[d] | 4.0 |

TABLE VI

| Ingredient | weight percent of total composition |
|---|---|
| Compound No. 1 | 5.0 |
| Xylene | 65.0 |
| Hallcomid TM M8-10[b] | 20.0 |
| Tenseofix TM B7438[c] | 3.0 |
| Tenseofix TM B7453[c] | 3.0 |
| Ethomeen TM C25[d] | 4.0 |

TABLE VII

| Ingredient | weight percent of total composition |
|---|---|
| Compound No. 3 | 25.0 |
| Barden AG clay | 50.0 |
| Celite TM 209[e] | 17.0 |
| Nekal TM BA-75[f] | 3.0 |
| Daxad TM 21[g] | 5.0 |

TABLE VIII

| Ingredient | weight percent of total composition |
|---|---|
| Compound No. 4 | 50.0 |
| Barden AG clay | 21.0 |
| Celite TM 209[e] | 21.0 |
| Polyfon TM H[h] | 5.0 |
| Aerosol TM OTB[i] | 3.0 |

TABLE IX

| Ingredient | weight percent of total composition |
|---|---|
| Compound No. 2 | 50.0 |
| Barden AG clay | 21.0 |
| Celite TM 209[e] | 21.0 |
| Polyfon TM H[h] | 5.0 |
| Aerosol TM OTB[i] | 3.0 |

Flowable Concentrate

TABLE X

| Ingredient | weight percent of total composition |
|---|---|
| Compound No. 3 | 12.0 |
| Pluronic TM P105[j] | 2.0 |
| Darvan TM #1[k] | 0.5 |
| Dow Corning TM FG10[m] | 1.0 |
| VeeGum TM[n] | 0.3 |
| Kelzan TM[o] | 0.04 |
| Propylene glycol | 4.5 |
| water | 79.66 |

TABLE XI

| Ingredient | weight percent of total composition |
|---|---|
| Compound No. 4 | 12.0 |
| Sun Spray TM 11N oil[p] | 72.7 |
| Bentone TM 38[q] | 1.0 |
| solution of 95% methanol/5% water | 0.3 |
| Emulsogen TM M[r] | 12.0 |
| Agrimul TM 70A[s] | 2.0 |

TABLE XII

| Ingredient | weight percent of total composition |
|---|---|
| Compound No. 1 | 12.0 |
| Pluronic TM P105[j] | 2.0 |
| Darvan TM #1[k] | 0.5 |
| Dow Corning TM FG10[m] | 1.0 |
| VeeGum TM[n] | 0.3 |
| Kelzan TM[o] | 0.04 |
| Propylene glycol | 4.5 |
| water | 79.66 |

Dusts

TABLE XIII

| Ingredient | weight percent of total composition |
|---|---|
| Compound No. 2 | 5.0 |
| Barden clay | 80.0 |
| Celite TM 209[e] | 15.0 |

TABLE XIV

| Ingredient | weight percent of total composition |
|---|---|
| Compound No. 4 | 2.5 |
| Barden clay | 82.5 |
| Celite TM 209[e] | 15.0 |

TABLE XV

| Ingredient | weight percent of total composition |
|---|---|
| Compound No. 3 | 5.0 |
| Barden clay | 80.0 |

TABLE XV-continued

| Ingredient | weight percent of total composition |
|---|---|
| Celite ™ 209[c] | 15.0 |

In the above Tables:
Aromatic 100 = an aromatic hydrocarbon solvent with a Flash point above 101° F. TCC, a product of Exxon Corp.
[a] an anionic/nonionic emulsifier product of Atlas Chemical Industries, Inc.
[b] N,N'-dimethyl amides of fatty acid, a product of The C. P. Hall Co.
[c] blends of calcium dodecylbenzenesulfonates with nonylphenol propylene oxide/ethylene oxide block copolymers, a product of Tenseia, Inc.
[d] is a proprietary material of Akzo Chemicals, Inc.
[e] diatomaceous earth, a product of Johns-Manville Products, Inc.
[f] sodium alkylnaphthalene sulfonate, an anionic emulsifier product of GAF Corp.
[g] a polyaryl and substituted benzoid alkylsulfonic acid, a product of W. R. Grace & Co.
[h] sugar-free, sodium based sulfonates of Kraft lignin is a proprietary material of West Virginia Pulp and Paper Co.
[i] dioctyl ester of sodium sulfosuccinic acid, a product of American Cyanamid Co.
[j] condensate of ethylene oxide with hydrophobic bases formed by condensing propylene oxide with propylene glycol, a product of BASF Corp.
[k] sodium salts of polymerized alkylnaphthalene sulfonic acid, an anionic surfactant of R. T. Vanderbilt Co., Inc.
[m] is a proprietary material of Dow Corning Corp.
[n] colloidal magnesium aluminum silicate, a product of R. T. Vanderbilt Co., Inc.
[o] a polysaccharide known as xanthan gum, a product of Kelco Co.
[p] a phytobland mineral oil also known as spray oil, a product of Sun Oil Co.
[q] organic derivative of hydrous magnesium aluminum silicate minerals, a product of National Lead Co.
[r] a nonionic ethoxylated derivative-a mineral oil emulsifier of American Hoechst Corp.
[s] alkyl aryl polyether alcohol, a product of Henkel Corp.

The following examples illustrates the herbicidal effects of the compounds of this invention.

The plant species employed in these evaluations were as follows:

| Common Name | Scientific Name |
|---|---|
| Barnyard grass | Echinochloa crusgalli |
| Yellow foxtail | Setaria lutescens |
| Johnson grass | Sorghum halepense |
| Wild Oat | Avena fatua |
| Cotton | Gossypium hirsutum |
| Oilseed rape | Brassica napus |
| Soybean | Glycine max |
| Sugarbeet | Beta vulgaris |
| Sunflower | Helianthus |

EXAMPLE XI

Pre-emergent Evaluation

In representative operations, each compound to be utilized in a series of tests is dissolved in acetone to one-half of the final volume (twice the final concentration) to be used and the acetone solution in each case is admixed with an equal volume of water containing 0.1 percent by weight of a non-ionic surfactant TWEEN ® 20 (a polyoxyethylene sorbitan monolaurate). The compositions, generally in the nature of an emulsion, were employed to spray seed beds of separate respective plant species which had been planted in soil of good nutrient content in a greenhouse. Sufficient amounts were employed to provide various application rates as listed in the table. The various beds were positioned side by side and exposed to substantially identical conditions of temperature and light. Each bed was maintained so as to prevent any interaction with test compounds in different seed beds. Other seed beds were treated with a acetone/TWEEN ® 20/water mixture containing no test compound to serve as controls. After treatment, the seed beds were maintained for about 2 weeks under greenhouse conditions conducive for good plant growth and watered as necessary. The specific plant species, test compound and dosage and the percent postemergent control obtained are set forth in Table XVI. Control refers to the reduction in growth compared to the observed results of the same untreated species. Note the "NT" means "not tested".

TABLE XVI

| Compound Tested | Dosage in lb/A | Percent pre-emergent kill and control of Plant Species |||||||||
|---|---|---|---|---|---|---|---|---|---|---|
| | | Cotton | Rape | Soybean | Sugar Beet | Sunflower | Yellow Foxtail | Johnson Grass | Barnyard Grass | Wild Oat |
| 1 | .50 | 0 | 0 | 0 | 0 | 0 | 100 | 100 | 100 | 100 |
|   | 1.0 | 0 | 0 | 0 | 0 | 0 | 100 | 100 | 100 | 100 |
| 2 | .5  | 0 | 0 | 0 | 0 | 0 | 100 | 100 | 100 | 100 |
|   | 1.0 | 0 | 0 | 0 | 0 | 0 | 100 | 100 | 100 | 100 |
| 4 | .5  | 0 | 0 | 0 | 0 | 0 | 100 | 100 | 100 | 100 |
|   | 1.0 | 0 | 0 | 0 | 0 | 0 | 100 | 100 | 100 | 100 |
| 5 | .25 | 0 | 0 | 0 | 0 | 0 | 10  | 95  | NT  | 0   |
|   | .5  | 0 | 0 | 0 | 0 | 0 | 50  | 95  | NT  | 20  |

EXAMPLE XII

Postemergent Evaluation

In representative operations, each compound to be utilized in a series of tests is dissolved in acetone to one-half of the final volume (twice the final concentration) to be used and the acetone solution in each case is admixed with an equal volume of water containing 0.1 percent by weight of a non-ionic surfactant TWEEN ® 20 (a polyoxyethylene sorbitan monolaurate). The compositions, generally in the nature of an emulsion, were employed to spray separate respective plant species which had been grown, in a greenhouse, to a height of 2-6 inches in soil of good nutrient content. Sufficient amounts were employed to provide various application rates as listed in the table. The various beds were positioned side by side and exposed to substantially identical conditions of temperature and light. Each bed was maintained so as to prevent any interaction with test compounds in different plant beds. Other plant beds were treated with a acetone/TWEEN ® 20/water mixture containing no test compound to serve as controls. After treatment, the plants were maintained for about 2 weeks under greenhouse conditions conducive for good plant growth and watered as necessary. The specific plant species, test compound and dosage and the percent postemergent control obtained are set forth in Table XVII. Control refers to the reduction in growth compared to the observed results of the same untreated species. Note the "NT" means "not tested."

TABLE XVII

| Compound Tested | Dosage in ppm | Percent postemergent kill and control of Plant Species | | | | | | | |
|---|---|---|---|---|---|---|---|---|---|
| | | Cotton | Rape | Soybean | Sugar Beet | Yellow Foxtail | Johnson Grass | Barnyard Grass | Wild Oat |
| 1 | 250 | 0 | 0 | 0 | 0 | 100 | 100 | 100 | 100 |
|   | 500 | 0 | 0 | 0 | 0 | 100 | 100 | 100 | 100 |
|   | 1000 | 0 | 0 | 0 | 0 | 100 | 100 | 100 | 100 |
| 2 | 250 | 0 | 0 | 0 | 0 | 90 | 90 | 100 | 100 |
|   | 500 | 0 | 0 | 0 | 0 | 100 | 100 | 100 | 100 |
|   | 1000 | 0 | 0 | 0 | 0 | 100 | 100 | 100 | 100 |
| 4 | 250 | 0 | 0 | 0 | 0 | 100 | 100 | 100 | 100 |
|   | 500 | 0 | 0 | 0 | 0 | 100 | 100 | 100 | 100 |
|   | 1000 | 0 | 0 | 0 | 0 | 100 | 100 | 100 | 100 |
| 5 | 62.5 | 0 | 0 | 0 | 0 | 20 | 30 | 30 | 70 |
|   | 125 | 0 | 0 | 0 | 0 | 70 | 70 | 60 | 60 |
|   | 250 | 0 | 20 | | | 80 | 85 | 70 | 70 |

Other compounds, not exemplified, but within the scope of the present invention may also be employed in the same manner as set forth hereinabove to control certain plant species with results commensurate to the above described results.

Various modifications may be made in the present invention without departing from the spirit or scope thereof and it is understood that we limit ourselves only as defined in the appended claims.

What is claimed is:

1. A substituted cyclohexanedione compound corresponding to the formula

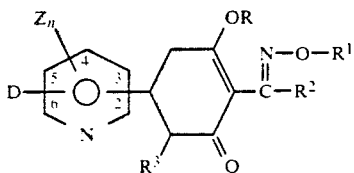

wherein

D is a group corresponding to one of the formulae,

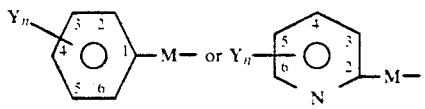

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen, $C_1$-$C_4$ alkyl or $C_1$-$C_4$ alkoxycarbonyl;

each Z independently represents hydrogen, halo, $C_1$-$C_4$ alkyl, $C_1$-$C_4$ alkoxy or —$CF_3$;

M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl; and n represents the integer 1, 2 or 3;

or a herbicidally acceptable organic or inorganic salt thereof.

2. A compound as defined in claim 1 wherein D is

3. A compound as defined in claim 2 wherein R is hydrogen.

4. The compound as defined in claim 3 which is 2-((1-ethoxyimino)propionyl)-3-hydroxy-5-(6-(4-(methylthio)phenoxy)-2-pyridyl)cyclohex-2-en-1-one.

5. The compound as defined in claim 3 which is 2-((1-ethoxyimino)propionyl)-3-hydroxy-5-(6-(4-(methylsulfinyl)phenoxy)-2-pyridyl)cyclohex-2-en-1-one.

6. The compound as defined in claim 3 which is 2-((1-ethoxyimino)propionyl)-3-hydroxy-5-(6-(4-(methylsulfonyl)phenoxy)-2-pyridyl)cyclohex-2-en-1-one.

7. The compound as defined in claim 3 which is 2-((1-ethoxyimino)propionyl)-3-hydroxy-5-(6-(4-(methylthio)phenylthio)-2-pyridyl)cyclohex-2-en-1-one.

8. The compound as defined in claim 3 which is 2-((1-ethoxyimino)propionyl)-3-hydroxy-5-(6-(2,4-dichlorophenoxy)-2-pyridyl)cyclohex-2-en-1-one.

9. A compound as defined in claim 1 wherein D is

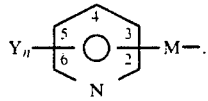

10. A herbicidal composition which comprises an inert carrier in intimate admixture with a herbicidally effective amount of an active ingredient which is a substituted cyclohexanedione compound corresponding to the formula

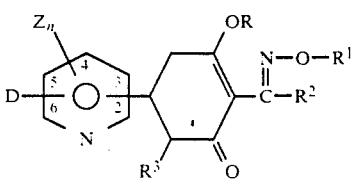

wherein

D is a group corresponding to one of the formulae,

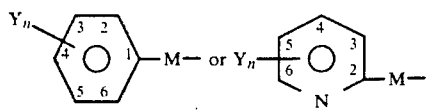

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R^1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen, $C_1$-$C_4$ alkyl or $C_1$-$C_4$ alkoxycarbonyl;

each Z independently represents hydrogen, halo, $C_1$-$C_4$ alkyl, $C_1$-$C_4$ alkoxy or —$CF_3$;

M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CF_3$, with the proviso that when M is =S(O), Y cannot be $C_1$-$C_4$ alkylthio and when M is =S(O)$_2$, Y cannot be $C_1$-$C_4$ alkylthio or $C_1$-$C_4$ alkylsulfinyl; and n represents the integer 1, 2 or 3;

and the herbicidally acceptable organic and inorganic salts thereof.

11. A composition as defined in claim 10 wherein D is

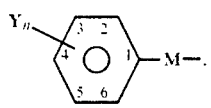

12. A composition as defined in claim 11 wherein R is hydrogen.

13. The composition as defined in claim 12 wherein the active ingredient is 2-((1-ethoxyimino)propionyl)-3-hydroxy-5-(6-(4-(methylthio)phenoxy)-2-pyridyl)cyclohex-2-en-1-one.

14. The composition as defined in claim 12 wherein the active ingredient is 2-((1-ethoxyimino)propionyl)-3-hydroxy-5-(6-(4-(methylsulfinyl)phenoxy)-2-pyridyl)-cyclohex-2-en-1-one.

15. The composition as defined in claim 12 wherein the active ingredient is 2-((1-ethoxyimino)-propionyl)-3-hydroxy-5-(6-(4-(methylsulfonyl)phenoxy)2--pyridyl)cyclohex-2-en-1-one.

16. The composition as defined in claim 12 wherein the active ingredient is 2-((1-ethoxyimino)propionyl)-3-hydroxy-5-(6-(4-(methylthio)phenylthio)-2-pyridyl)cyclohex-2-en-1-one.

17. The composition as defined in claim 12 wherein the active ingredient is 2-((1-ethoxyimino)propionyl)-3-hydroxy-5-(6-(2,4-dichlorophenoxy)-2-pyridyl)cyclohex-2-en-1-one.

18. A composition as defined in claim 10 wherein D is

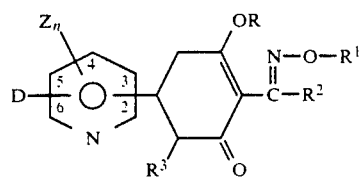

19. A method for the kill or control of grassy weeds which comprises contacting said weeds or their habitat with a herbicidally effective amount of a composition which comprises an inert carrier in intimate admixture with a herbicidally active ingredient which is a substituted cyclohexanedione compound corresponding to the formula

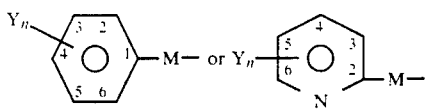

wherein
D is a group corresponding to one of the formulae,

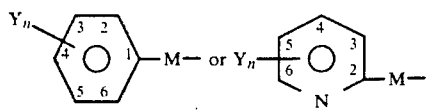

R represents hydrogen, $C_1$-$C_4$ alkyl, $C_1$-$C_4$ haloalkyl, $C_2$-$C_4$ alkenyl, $C_3$-$C_4$ alkynyl, $C_1$-$C_4$ alkylsulfonyl, phenylsulfonyl or acyl;

$R_1$ represents $C_1$-$C_4$ alkyl, $C_1$-$C_4$ haloalkyl, $C_2$-$C_4$ alkenyl, $C_2$-$C_4$ haloalkenyl, $C_3$-$C_4$ alkynyl, or $C_3$-$C_4$ haloalkynyl;

$R^2$ represents $C_1$-$C_4$ alkyl, $C_1$-$C_4$ fluoroalkyl, $C_1$-$C_4$ alkylthiomethyl, $C_1$-$C_4$ alkoxymethyl, $C_2$-$C_4$ alkenyl or $C_3$-$C_4$ alkynyl;

$R^3$ represents hydrogen, $C_1$-$C_4$ alkyl or $C_1$-$C_4$ alkoxycarbonyl;

each Z independently represents hydrogen, halo, $C_1$-$C_4$ alkyl, $C_1$-$C_4$ alkoxy or —$CF_3$ M represents =O, =S, =S(O) or =S(O)$_2$;

Y represents hydrogen, halo, $C_1$-$C_4$ alkyl, $C_1$-$C_4$ alkoxy, $C_1$-$C_4$ alkylthio, $C_1$-$C_4$ alkylsulfinyl or $C_1$-$C_4$ alkylsulfonyl or —$CH_3$, with the proviso that when M is =S(O), cannot be $C_1$-$C_4$ alkylthio and when M is =S(O)$_2$, Y cannot be $C_1$-$C_4$ alkylthio or $C_1$-$C_4$ alkylsulfinyl; and n represents the integer 1, 2 or 3;

and the herbicidally acceptable organic and inorganic salts thereof.

20. A method as defined in claim 19 wherein D is

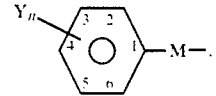

21. A method as defined in claim 20 wherein R is hydrogen.

22. The method as defined in claim 21 wherein the active ingredient is 2-((1-ethoxyimino)propionyl)-3-hydroxy-5-(6-(4-(methylthio)phenoxy)-2-pyridyl)cyclohex-2-en-1-one.

23. The method as defined in claim 21 wherein the active ingredient is 2-((1-ethoxyimino)propionyl)-3-hydroxy-5-(6-(4-(methylsulfinyl)phenoxy)-2-pyridyl)-cyclohex-2-en-1-one.

24. The method as defined in claim 21 wherein the active ingredient is 2-((1-ethoxyimino)propionyl)-3-hydroxy-5-(6-(4-(methylsulfonyl)phenoxy)-2-pyridyl)-cyclohex-2-en-1-one.

25. The method as defined in claim 21 wherein the active ingredient is 2-((1-ethoxyimino)propionyl)-3-hydroxy-5-(6-(4-(methylthio)phenylthio)-2-pyridyl)cyclohex-2-en-1-one.

26. The method as defined in claim 21 wherein the active ingredient is 2-((1-ethoxyimino)propionyl)-3-hydroxy-5-(6-(2,4-dichlorophenoxy)-2-pyridyl)cyclohex-2-en-1-one.

27. A method as defined in claim 19 wherein D is

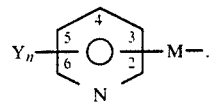

* * * * *